(12) United States Patent
Iwanaga et al.

(10) Patent No.: US 10,697,950 B2
(45) Date of Patent: *Jun. 30, 2020

(54) FLUORESCENT COMPOUND, FLUORESCENT COMPOUND MIXTURE, FRESHNESS MARKER, FRESHNESS LABEL, AND SENSING SYSTEM

(71) Applicants: KABUSHIKI KAISHA TOSHIBA, Tokyo (JP); TOSHIBA TEC KABUSHIKI KAISHA, Tokyo (JP)

(72) Inventors: Hiroki Iwanaga, Yokohama Kanagawa (JP); Ryozo Akiyama, Mishima Shizuoka (JP)

(73) Assignees: KABUSHIKI KAISHA TOSHIBA, Tokyo (JP); TOSHIBA TEC KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/516,671

(22) Filed: Jul. 19, 2019

(65) Prior Publication Data

US 2019/0339245 A1 Nov. 7, 2019

Related U.S. Application Data

(63) Continuation of application No. 15/491,568, filed on Apr. 19, 2017, now Pat. No. 10,444,214.

(30) Foreign Application Priority Data

Jan. 25, 2017 (JP) ................................. 2017-011618

(51) Int. Cl.
| | |
|---|---|
| *G01N 21/64* | (2006.01) |
| *G01N 33/12* | (2006.01) |
| *C09K 11/06* | (2006.01) |
| *C09B 23/14* | (2006.01) |
| *G09F 3/00* | (2006.01) |

(52) U.S. Cl.
CPC ........... *G01N 33/12* (2013.01); *C09B 23/148* (2013.01); *C09K 11/06* (2013.01); *G01N 21/6428* (2013.01); *C09K 2211/1007* (2013.01); *G01N 2021/6439* (2013.01); *G09F 3/0291* (2013.01); *Y10T 436/173845* (2015.01)

(58) Field of Classification Search
None
See application file for complete search history.

(56) References Cited

U.S. PATENT DOCUMENTS

| | | | | |
|---|---|---|---|---|
| 10,444,214 | B2 * | 10/2019 | Iwanaga | G01N 33/12 |
| 2014/0328764 | A1 * | 11/2014 | Tang | C09K 11/06 |
| | | | | 424/9.6 |
| 2017/0160270 | A1 | 6/2017 | Iwanaga et al. | |

FOREIGN PATENT DOCUMENTS

| | | |
|---|---|---|
| JP | 2012051816 A | 3/2012 |
| JP | 2013234221 A | 11/2013 |
| JP | 2014012654 A | 1/2014 |
| JP | 5934570 B2 | 6/2016 |

OTHER PUBLICATIONS

Mei, J. et al. "Aggregation-Induced Emission: Together We Shine, United We Soar!" Chem. Rev. 2015, 115, 11718-11940. (Year: 2015).*

Leigh, W.J. et al., "Merostabilization in radical ions, triplets, and biradicals. 5. The thermal cis-trans isomerization of para-substituted tetraphenylethylene," Can. J. Chem vol. 59, 1981, 609-620. (Year: 1981).

Liang, J. et al., "Distinct optical and kinetic responses from E/Z isomers of caspase probes with aggregation-induced emission characteristics,"J. Mater. Chem. B, 2014, 2, 4363-4370; including Electronic Supplementary Information. (Year: 2014).

Mitsutaka Nakamura et al., "Fluorometric Sensing of Biogenic Amines with Aggregation-induced Emission-Active Tetraphenylethenes", Chem. Eur. J. 2011, 17, pp. 5344-5349.

* cited by examiner

*Primary Examiner* — Christopher Adam Hixson
*Assistant Examiner* — Michelle Adams
(74) *Attorney, Agent, or Firm* — Kim & Stewart LLP

(57) ABSTRACT

Disclosed herein is a fluorescent compound represented by the following general formula and having fluorescence characteristics that vary in the presence of a subject substance,

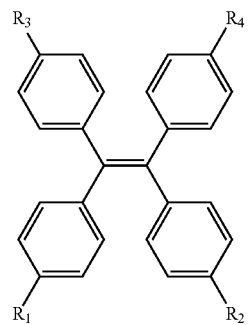

wherein $R_1$ and $R_2$ each independently represent a carboxyl group, or a substituent containing a carboxyl group, and $R_3$ and $R_4$ each independently represent a hydrogen atom, an alkyl group, an alkoxy group, a halogen atom, a hydroxyl group, a carboxyl group, or a substituent containing a carboxyl group.

20 Claims, 9 Drawing Sheets

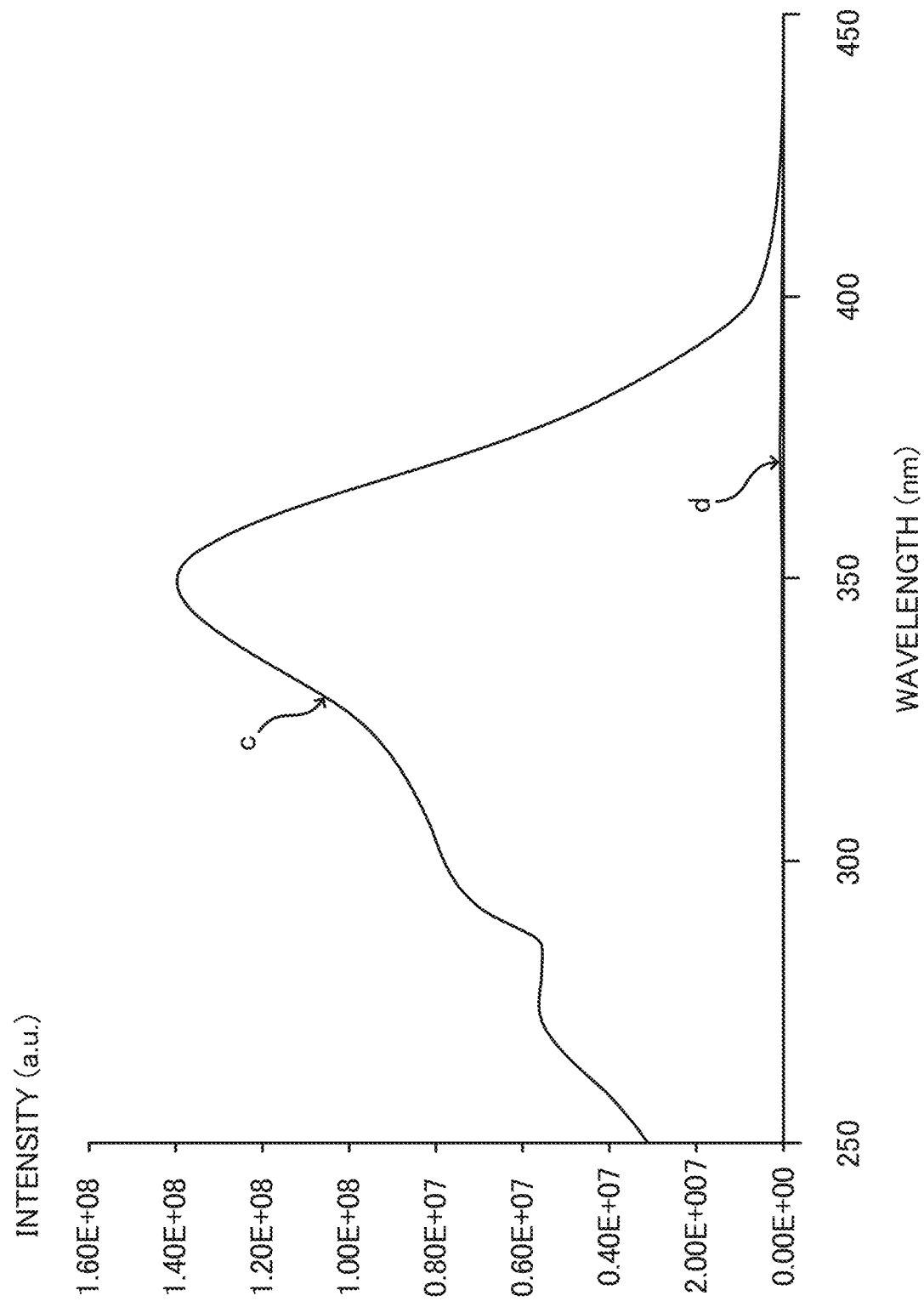

FIG. 9

| | DAY 1 | DAY 2 | DAY 3 | DAY 4 | DAY 5 |
|---|---|---|---|---|---|
| BOTTLE D (KAMABOKO) | COMPARATIVE EXAMPLE 2 | | | | |
| | COMPARATIVE EXAMPLE 3 | | | | |
| | EXAMPLE 4 | | | | |
| | EXAMPLE 5 | | | | |

FLUORESCENT COMPOUND, FLUORESCENT COMPOUND MIXTURE, FRESHNESS MARKER, FRESHNESS LABEL, AND SENSING SYSTEM

CROSS-REFERENCE TO RELATED APPLICATIONS

This application is a continuation of U.S. patent application Ser. No. 15/491,568, filed on Apr. 19, 2017, which is based upon and claims the benefit of priority from Japanese Patent Application 2017-011618 filed on Jan. 25, 2017, the entire contents of each of which are incorporated herein by reference.

FIELD

Embodiments described herein relate generally to a fluorescent compound, a fluorescent compound mixture, a freshness marker, a freshness label, and a sensing system.

BACKGROUND

Amines generated by food spoilage (hereinafter, referred to as "biogenic amines", or, simply, "amines") in aquatic and meat products pose health risks such as allergic disease and food poisoning. Biogenic amines are produced by decarboxylation reaction of amino acid, and generate also during processing or storage of food. The amount of generated biogenic amine can thus be used as an index of freshness in food. For the prevention of allergic disease and food poisoning, and the reduction of food waste, there is a need for a method for sensing biogenic amine with high sensitivity and high selectivity.

Known biogenic amine sensing methods use analytical instruments such as gas chromatography and liquid chromatography devices. However, sensing methods using such analytical instruments take time because these methods require processing before measurement, and the devices need to be constantly monitored for adjustment. These add to the cost of the sensing methods using analytical instruments.

A method using a tetraphenylethene fluorescent compound is proposed as an easy and quick biogenic amine sensing method. This sensing method uses a solution of tetraphenylethene fluorescent compound. Dissolving a biogenic amine in the solution causes the tetraphenylethene fluorescent compound to react with the biogenic amine, and form an aggregate in the solution. The tetraphenylethene fluorescent compound produces only a weak fluorescence intensity by itself, but is known to produce a stronger fluorescence intensity upon forming an aggregate. An increased fluorescence intensity can be detected as an indication of biogenic amine generation. The detection result can then be determined as sensing of deterioration of freshness in food. However, the sensitivity to biogenic amine is still insufficient.

DESCRIPTION OF THE DRAWINGS

FIG. 3 is a graph representing an example of a fluorescence intensity change before and after formation of an aggregate by a freshness marker according to an exemplary embodiment.

FIG. 9 is an image showing fluorescence states of freshness labels according to an exemplary embodiment.

DETAILED DESCRIPTION

Figure 1A:
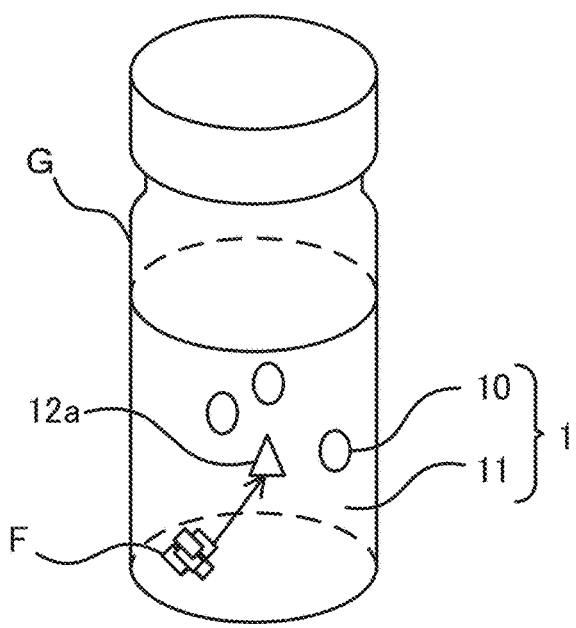
FIG. 1A is a diagram representing an example of a biogenic amine sensing process using a freshness marker according to an exemplary embodiment.

A fluorescent compound according to an embodiment is represented by the following general formula (1), and has fluorescence characteristics that vary in the presence of a subject substance.

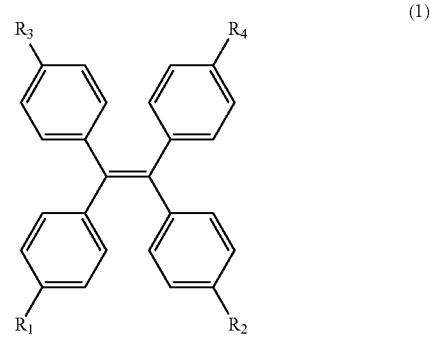

(1)

In the formula, $R_1$ and $R_2$ each independently represent a carboxyl group, or a substituent containing a carboxyl group. $R_3$ and $R_4$ each independently represent a hydrogen atom, an alkyl group, an alkoxy group, a halogen atom, a hydroxyl group, a carboxyl group, or a substituent containing a carboxyl group.

The embodiment is described below in detail with reference to the accompanying drawings. The embodiment is based on a fluorescent compound that is either a cis-tetraarylethene derivative or a trans-tetraarylethene derivative. The tetraarylethene derivative aggregates, and its fluorescence characteristics vary in the presence of an amine. The fluorescent compound according to the embodiment undergoes a larger fluorescence intensity change upon aggregation than a tetraarylethene derivative containing a cis-tetraarylethene derivative and a trans-tetraarylethene derivative in the same fraction. This makes it easier to observe a fluorescence intensity upon aggregation.

Biogenic Amine

If left unchecked, food typically undergoes changes in quality such as smell, appearance, texture, and taste over time before it is no longer suited for consumption. Such degeneration of food condition is called deterioration, decaying, or degradation, or, more commonly, "food spoilage". Food deterioration is caused by microorganisms, insects, self-digestion, chemical (lipid oxidation, browning), or physical (damage such as cuts and crushes) causes. In many cases, food deterioration is caused by proliferation of microorganisms (putrefactive bacteria). In a broad sense, the term "spoilage" is used to describe such deterioration of food by proliferation of microorganisms to the point where it is no longer edible.

Spoilage refers to the process by which protein in food decomposes by the effects of microorganisms, and produces harmful substances or a bad odor. This is often distinguished from "decaying", which describes a state in which carbohydrates and fats decompose by the effects of microorganisms, and produce a bad flavor not suitable for consumption. The term "degradation" describes a state where such spoilage or decaying makes the food not suitable for consumption. The main components of a foul odor are various amine components also called biogenic amines such as ammonia, and trimethylamine.

The nitrogen compounds in food are mainly proteins, which become hydrolyzed by the enzymes of microorganisms and food into polypeptides, and to simple peptides or amino acids. These amino acids decompose through reactions such as deamination, transamination, and decarboxylation, and produce biogenic amines.

Examples of the biogenic amines produced by amino acids include 1,2-ethylenediamine, 1,3-propanediamine, 1,4-butanediamine, 1,5-pentanediamine, 1,6-hexanediamine, spermidine, spermine, histamine, and tryptamine.

Fluorescent Compound

The fluorescent compound according to the embodiment aggregates, or precipitates into crystals in the presence of an amine, and changes its fluorescence characteristics, including fluorescence or excitation spectrum characteristics, and fluorescence lifetime. The fluorescent compound emits weak fluorescence when exposed to excitation light in a dissolved state in a solvent. The fluorescence intensity increases as the fluorescent compound according to the embodiment aggregates in the solvent.

Specifically, the fluorescent compound according to the embodiment is a simple tetraarylethene derivative represented by the following general formula (1) or (2), or a mixture of tetraarylethene derivatives represented by the following general formulae (1) and (2).

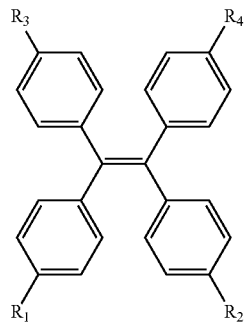
(1)

In the general formula (1), $R_1$ and $R_2$ each independently represent a carboxyl group, or a substituent containing a carboxyl group. $R_3$ and $R_4$ each independently represent a hydrogen atom, an alkyl group, an alkoxy group, a halogen atom, a hydroxyl group, a carboxyl group, or a substituent containing a carboxyl group.

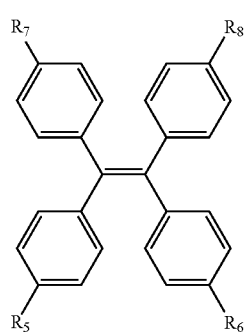
(2)

In the general formula (2), $R_5$ and $R_8$ each independently represent a carboxyl group, or a substituent containing a carboxyl group. $R_6$ and $R_7$ each independently represent a hydrogen atom, an alkyl group, an alkoxy group, a halogen atom, a hydroxyl group, a carboxyl group, or a substituent containing a carboxyl group.

The tetraarylethene derivatives represented by the foregoing formulae (1) and (2) are synthesized from a compound represented by the following general formula (3), using a known reaction technique. For synthesis of the tetraarylethene derivative, the compounds represented by the following general formula (3) may be used as a mixture of two or more, as required.

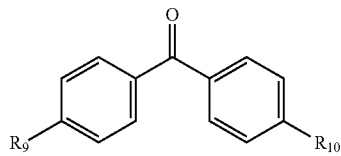
(3)

In the general formula (3), $R_9$ represents a carboxyl group, or a substituent containing a carboxyl group. $R_{10}$ represents a hydrogen atom, an alkyl group, an alkoxy group, a halogen atom, a hydroxyl group, a carboxyl group, or a substituent containing a carboxyl group.

In the embodiment, non-limiting examples of the substituent containing a carboxyl group include $-(CH_2)_m-$ COOH, —O—(CH$_2$)$_n$—COOH, —S—(CH$_2$)$_m$—COOH, —NH—(CH$_2$)$_m$—COOH, —O—(CH$_2$)$_m$—S—(CH$_2$)$_n$—COOH, —O—(CH$_2$)$_m$—NH—(CH$_2$)$_m$—COOH, —S—(CH$_2$)$_m$—O—(CH$_2$)$_n$—COOH, —S—(CH$_2$)$_m$—NH—(CH$_2$)$_m$—COOH, —NH—(CH$_2$)$_m$—O—(CH$_2$)$_n$—COOH, and —NH—(CH$_2$)$_m$—S—(CH$_2$)$_n$—COOH (where m and n represent an integer of 1 to 6).

In the embodiment, non-limiting examples of the alkyl group include linear or branched alkyl groups of 1 to 6 carbon atoms, for example, such as methyl, ethyl, n-propyl, isopropyl, n-butyl, isobutyl, s-butyl, t-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 1-ethylbutyl, and 2-ethylbutyl.

In the embodiment, non-limiting examples of the alkoxy include linear or branched alkoxy of 1 to 6 carbon atoms, for example, such as methoxy, ethoxy, n-propoxy, isopropoxy, n-butoxy, isobutoxy, tert-butoxy, sec-butoxy, n-pentyloxy, isopentyloxy, neopentyloxy, n-hexyloxy, isohexyloxy, and 3-methylpentyloxy.

When $R_9$ and $R_{10}$ in the compound represented by the general formula (3) are different substituents, the synthesized tetraarylethene derivative has cis and trans isomers (geometric isomers). The tetraarylethene derivative is a mixture of the tetraarylethene derivatives represented by the general formulae (1) and (2), and the tetraarylethene derivatives represented by the general formulae (1) and (2) are cis and trans isomers.

In the mixture of tetraarylethene derivatives, the tetraarylethene derivative represented by the general formula (1) is a cis-fluorescent compound, and the tetraarylethene derivative represented by the general formula (2) is a trans-fluorescent compound.

As a rule, a cis-form has two substituents on the same side of the double bond, whereas a trans form has two substituents on the opposite sides of the double bond. As used herein, "cis-fluorescent compound" refers to a fluorescent compound that has a carboxyl group, or a substituent containing a carboxyl group disposed on the adjacent benzene rings. On the other hand, "trans-fluorescent compound" as used herein refers to a fluorescent compound that has a carboxyl group, or a substituent containing a carboxyl group on benzene rings that are on opposite sides of the double bond.

As a rule, cis and trans isomers are obtained as an equimolar mixture of cis and trans isomers. Accordingly, the tetraarylethene derivative mixture obtained after the synthesis contains the same number of moles of the cis-fluorescent compound and the trans-fluorescent compound represented by the general formulae (1) and (2), respectively. By separation and purification of the tetraarylethene derivative mixture, a tetraarylethene derivative of primarily the cis-fluorescent compound represented by the general formula (1), or a tetraarylethene derivative of primarily the trans-fluorescent compound represented by the general formula (2) can be obtained.

The tetraarylethene derivatives represented by the general formulae (1) and (2) produce weak fluorescence in a dissolved state in a solvent. In the presence of an amine, the tetraarylethene derivative aggregates as it becomes less soluble in solution through hydrogen bonding or electrostatic interaction (hereinafter, also referred to as "reaction") of the carboxyl group in the molecule with the amine. The aggregated tetraarylethene derivative emits fluorescence of higher fluorescence intensity when exposed to excitation light such as ultraviolet (UV) light. This change in the fluorescence characteristics occurs as the aggregation of the tetraarylethene derivative restricts the aryl rotation in the tetraarylethene derivative. In the embodiment, the fluorescent compound is dissolved in a solvent in such a concentration that the unreacted fluorescent compound does not aggregate or precipitate, or does not become saturated.

A tetraarylethene derivative solution prepared by dissolving the tetraarylethene derivative in a solvent produces fluorescence of high fluorescence intensity in the presence of an amine. Observed changes in the fluorescence intensity of the fluorescence produced by the solution can thus be detected as an indication of the presence of an amine.

Freshness Marker

The fluorescent compound according to the embodiment may be used for a freshness marker. The freshness marker includes the fluorescent compound according to the embodiment, and a solvent dissolving the fluorescent compound according to the embodiment.

Solvent

The solvent according to the embodiment is a solvent capable of dissolving the fluorescent compound, and having good compatibility with the biogenic amine to be sensed. Use of a solvent that is poorly compatible with the biogenic amine may result in formation of heterogeneous aggregates, and cause poor freshness marker sensitivity.

Because the freshness marker is used to sense deterioration of food over time, the solvent according to the embodiment is preferably a solvent that does not undergo evaporative volume reductions in the atmosphere over a certain length of time. Further, because the freshness marker is used by being attached to food or being installed in the vicinity of food, the solvent according to the embodiment is preferably a solvent that is safe to the human body. The solvent according to the embodiment may be a mixed solvent of two or more solvents.

Preferred as such a solvent is a glycol-based solvent having a high boiling point and low toxicity. Specific examples of such glycol-based solvents include ethylene glycol-based solvents such as polyethylene glycol monomethyl ether, diethylene glycol ethyl methyl ether, polyethylene glycol dimethyl ether, triethylene glycol butyl methyl ether, and diethylene glycol butyl methyl ether; and propylene glycol-based solvents such as propylene glycol monomethyl ether, propylene glycol monobutyl ether, and propylene glycol dimethyl ether.

The freshness marker according to the embodiment may be used as, for example, a spoiled substance detection chemical solution for detecting a spoiled substance.

Figure 1B:
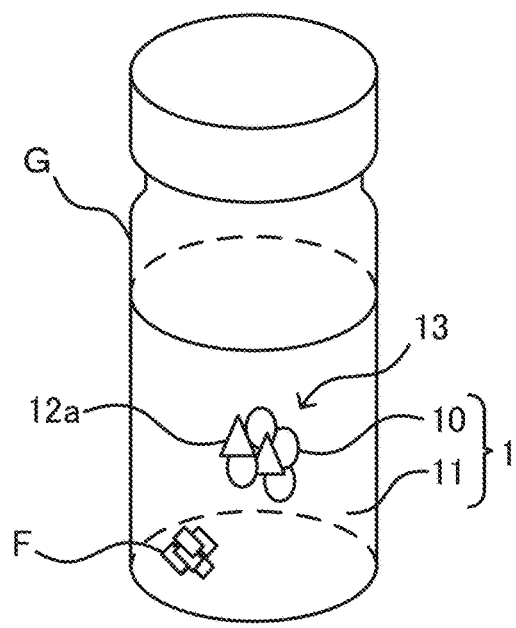
FIG. 1B is a diagram representing an example of a biogenic amine sensing process using a freshness marker according to an exemplary embodiment.

FIGS. 1A and 1B are diagrams representing an example of a biogenic amine sensing process using the freshness marker according to the embodiment. As illustrated in FIG. 1A, a freshness marker 1 according to the embodiment includes a fluorescent compound 10, and a solvent 11 dissolving the fluorescent compound 10. The freshness marker 1 according to the embodiment is contained in a glass container G. As illustrated in FIG. 1B, a biogenic amine 12*a* in biogenic amines generated from a food product F has good compatibility with the solvent 11, and forms an aggregate 13 with the fluorescent compound 10 dissolved in the solvent 11. The freshness of the food product F can be determined by irradiating excitation light such as UV light to the freshness marker 1 from outside of the glass container G.

The freshness marker 1 has use for, for example, a spot test in a food factory. The freshness of the subject food product F can be determined by immersing a portion of the food product F in the freshness marker 1 contained in the glass container G. The food product F being tested contacts the freshness marker 1, and the fluorescent compound 10 in the freshness marker 1 quickly forms the aggregate 13 by reacting with a biogenic amine.

The freshness of the food product F also can be determined without immersing the food product F in the freshness marker 1. The freshness marker 1 may be used by being added to the food product F, or by being installed in the vicinity of the food product F. In the case of the freshness marker 1 installed in the vicinity of the food product F, the fluorescent compound reacts with biogenic amine vapor upon generation of biogenic amine from a spoiled food product F, and emits high-intensity fluorescence. A change in fluorescence intensity can be detected as an indication of biogenic amine generation to determine the freshness of the food product F.

Freshness Label

Figure 2A:
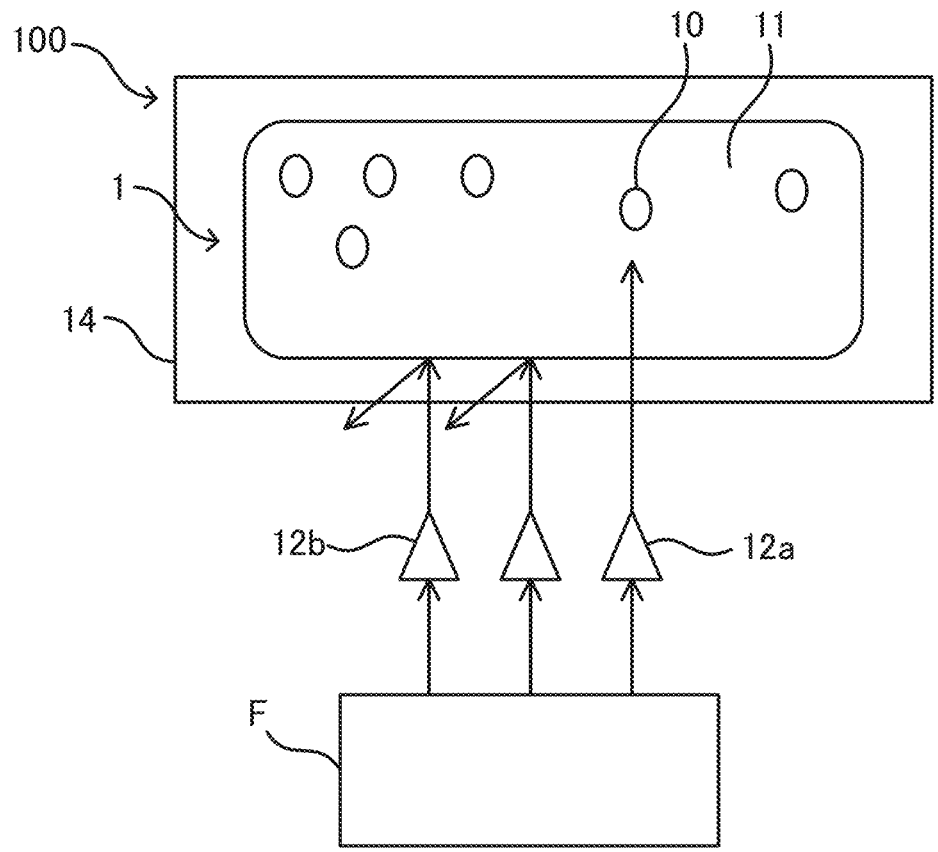
FIG. 2A is a diagram representing an example of a biogenic amine sensing process using a freshness label according to an exemplary embodiment.
Figure 2B:
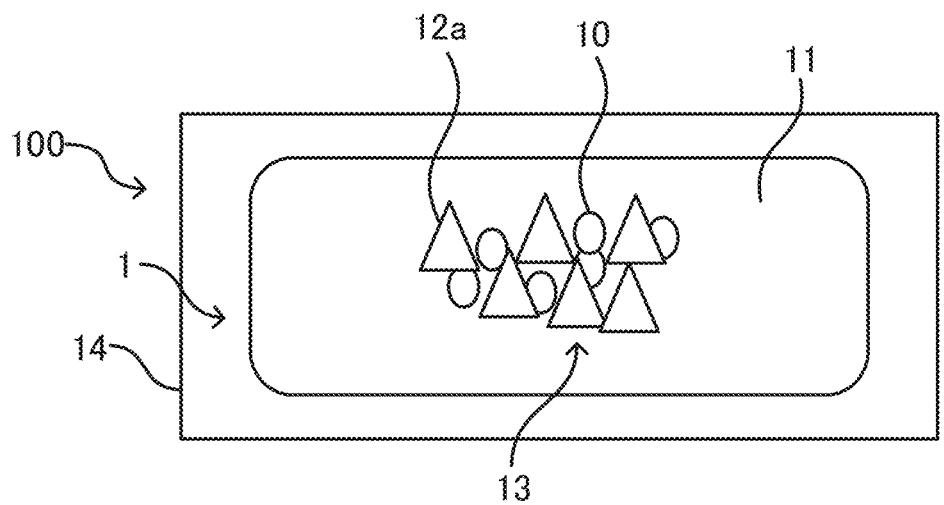
FIG. 2B is a diagram representing an example of a biogenic amine sensing process using a freshness label according to an exemplary embodiment.

The freshness marker 1 can be used to provide a freshness label. FIGS. 2A and 2B are diagrams representing an example of a biogenic amine sensing process using the freshness label according to the embodiment. A freshness label 100 is used for the detection of a biogenic amine generated from a food product F.

As illustrated in FIG. 2A, the freshness label 100 according to the embodiment includes medium 14 impregnated with the freshness marker 1 that includes the fluorescent compound 10 and the solvent 11.

Medium

The medium 14 according to the embodiment can retain the freshness marker 1. Considering retention of the freshness marker 1, the medium 14 is preferably one with a certain level of porosity, for example, a porous substrate, or a mesh structure.

Examples of such medium 14 include a cellulose fiber, paper, a fabric, a filter, and a sponge. Particularly preferred is a cellulose acetate membrane filter because it can enhance fluorescence intensity.

Preferably, the medium 14 is selected from materials having refractive indices as close as possible to the refractive index of the solvent 11 of the embodiment. With the medium 14 and the solvent 11 having similar refractive indices, the fluorescence generated inside the medium 14 will not be blocked. This makes it possible to obtain even higher fluorescence intensity, and the freshness marker 1 using the medium 14 is advantageous for freshness determination.

The freshness label is disposed near the food product F, for example. As illustrated in FIG. 2B, the food product F generates biogenic amines 12a and 12b, and the biogenic amine 12a having good compatibility with the solvent 11 forms the aggregate 13 with the fluorescent compound 10 retained in the medium 14. The freshness of the food product F can be determined by irradiating excitation light such as UV light to the freshness label 100.

The food product F, which is a food material such as fish and meat, is handled by, for example, being sealed (air tight) in a plastic container. The freshness of the food product F can be determined from outside of the container by attaching the freshness label 100 inside the container containing the food product F. The fluorescent compound 10 aggregates as it reacts with the biogenic amine 12a generated from the food product F. The freshness of the food product F can be determined by irradiating excitation light such as UV light to the freshness label 100 from outside of the container containing the food product F, without leaking air from the container.

Base Material

A base material that supports the freshness marker 1 or the freshness label 100 may be used, as required. Preferably, the base material is selected from materials that are resistant to the solvent 11 dissolving the fluorescent compound 10, and that do not emit fluorescence by themselves. However, the base material is not limited to such materials, and any material may be used with the provision that the fluorescence wavelength is not close to the fluorescence wavelength of the fluorescent compound 10 emitting fluorescence.

Examples of such base materials include plastic sheets such as a Teflon® sheet, a polyimide sheet, a polyester film, a polyacetal sheet, a nylon sheet, a polycarbonate sheet, a polypropylene sheet, a polyethylene sheet, a PET film, and a vinyl chloride sheet; and glass plates.

Determination Method

The freshness marker 1 according to the embodiment is used to determine the freshness of a food product F by sensing changes in the fluorescence characteristics of the fluorescent compound 10, as described above. The freshness marker 1 according to the embodiment may be used for a sensing system for sensing a subject substance.

A sensing system according to the embodiment is configured from the freshness marker according to the embodiment, a ultraviolet source unit that irradiates UV light to the freshness marker, and an emission detector that detects an image pattern that occurs in the freshness marker upon irradiation of the freshness marker with UV light. The sensing system according to the embodiment senses a subject substance using an image pattern that occurs in the freshness marker upon irradiation of the freshness marker with UV light, and enables determination of the freshness of a food product. Here, the emission detector means an imaging device such as a digital camera.

Specifically, a food product F is placed in the freshness marker 1. The freshness marker 1 is then irradiated with UV light using the ultraviolet source, and imaged with a digital camera. This can produce an image of the freshness marker 1.

The fluorescent compound 10 of the freshness marker 1 that reacted with the biogenic amine 12a generated from the food product F shows a fluorescence characteristics change. The freshness of the food product F can thus be determined from changes occurring in, for example, the color, and the luminance of the freshness marker 1 in the produced image. The determination of the freshness of the food product F may be made with a program that automatically determines, for example, the color, and the luminance of the freshness marker 1 appearing in the image. The program may be provided in the emission detector.

The electronic image produced by a digital camera or other such devices may be processed to enhance contrast. Such image processing is effective when a slight difference in fluorescence intensity, specifically, a slight difference in the amount of generated biogenic amine needs to be distinguished. It is also possible to use, for example, a smartphone with a camera having a colorimetric function, and automatically determine a fluorescence intensity difference in the image for determination of the freshness of a food product F.

The freshness of a food product F also may be determined by visually inspecting the freshness marker 1. When determining the freshness of a food product F through visual inspection, it is desirable to observe the freshness marker 1 in an environment where the influence of visible light is minimal, such as in a darkroom. The accuracy of freshness determination can improve when a fluorescence photometer is used.

Fluorescence Characteristics Changes

The fluorescent compound 10 is synthesized from the compound represented by the general formula (3). When the substituents $R_9$ and $R_{10}$ of the compound are different, the fluorescent compound is a mixture of a cis-fluorescent compound and a trans-fluorescent compound. In the fluorescent compound 10 of the freshness marker 1, the cis-fluorescent compound and the trans-fluorescent compound forms an assembly. An assembly of cis-fluorescent compound and trans-fluorescent compound fluoresces as the aryl rotation is restricted. This causes the freshness marker 1 to emit fluorescence even before forming the aggregate 13.

In the presence of the biogenic amine 12a, the fluorescent compound 10 fluoresces by forming the aggregate 13 through reaction with the biogenic amine 12a. That is, the freshness marker 1 also emits fluorescence after forming the aggregate 13.

FIG. 3 is a graph representing an example of the fluorescence intensity of the freshness marker 1 before and after formation of the aggregate 13. The fluorescent compound 10 of the freshness marker 1 is 95 mol % cis-fluorescent compound and 5 mol % trans-fluorescent compound. The measured characteristics curve c represents the relationship between the fluorescence intensity of the freshness marker 1 and wavelength after the formation of the aggregate 13 with a 6 molar equivalent of spermidine added to the freshness marker 1. The measured characteristics curve d represents the relationship between the fluorescence intensity of the freshness marker 1 and wavelength before formation of the aggregate 13. By comparing the characteristics curve c and the characteristics curve d, the fluorescence intensity represented by the characteristics curve c is higher than the fluorescence intensity represented by the characteristics curve d.

The fluorescence emitted by the freshness marker 1 becomes more clearly observable as the fluorescence intensity a of the fluorescence emitted by the freshness marker 1 after the formation of the aggregate 13 increases. The freshness marker 1 emitting fluorescence of high fluorescence intensity a is therefore advantageous for freshness determination. A fluorescence intensity change in the fluorescence emitted by the freshness marker 1 also becomes more clearly observable as the ratio of fluorescence intensity a increases relative to the fluorescence intensity b of the fluorescence emitted by the freshness marker 1 before formation of the aggregate 13. The freshness marker 1 emitting fluorescence with a larger ratio of fluorescence intensity a relative to fluorescence intensity b is therefore advantageous for freshness determination.

Figure 4:
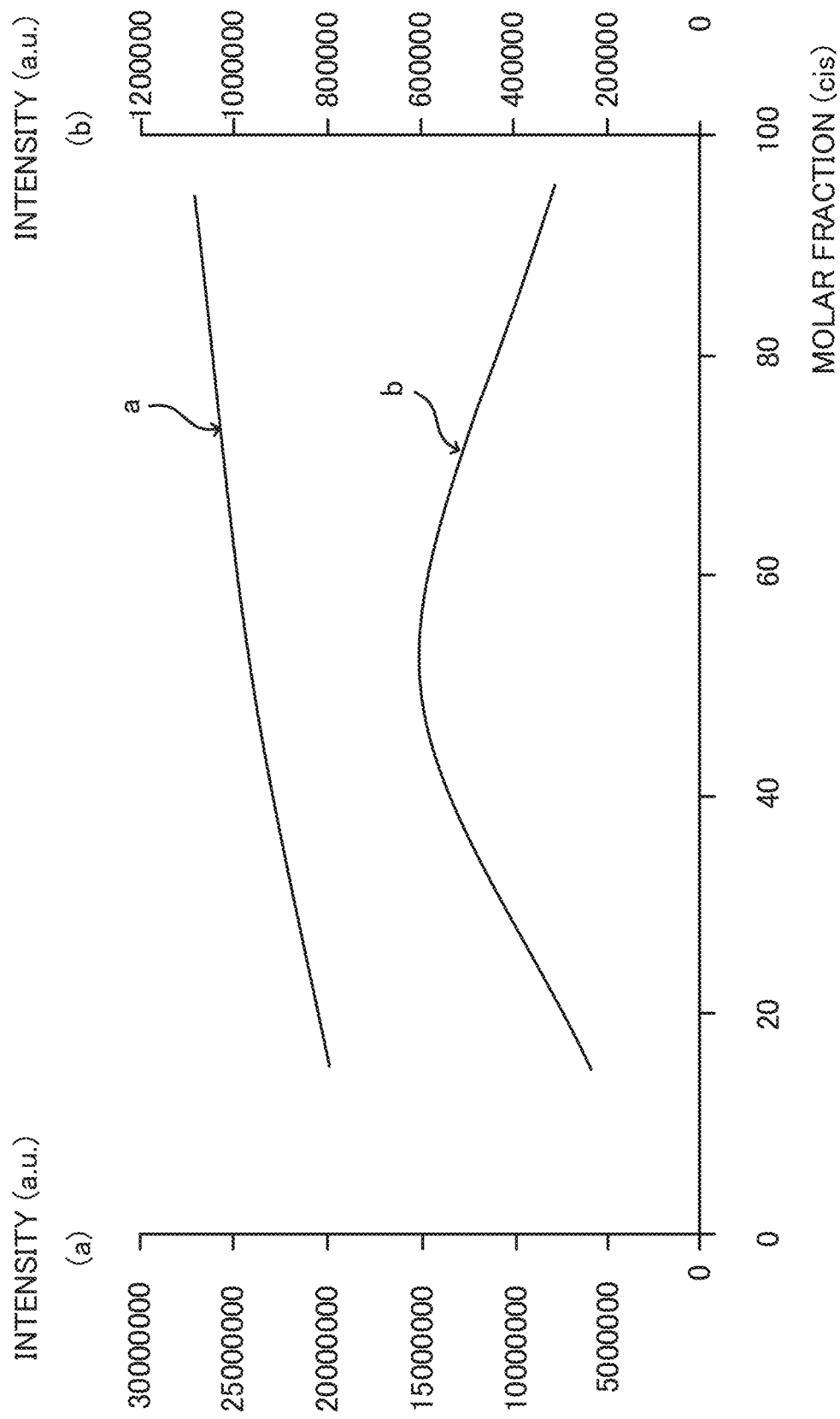
FIG. 4 is a diagram representing the relationship between fluorescence intensity and the fraction of cis-fluorescent compounds in a fluorescent compound of an Example.

FIG. 4 is a graph representing the relationship between fluorescence intensity and the fraction of cis-fluorescent compounds in the fluorescent compound 10. In FIG. 4, the left vertical axis represents the fluorescence intensity a of the fluorescence emitted by the freshness marker 1 after the formation of the aggregate 13, and the right vertical axis represents the fluorescence intensity b of the fluorescence emitted by the freshness marker 1 before formation of the aggregate 13. As shown in FIG. 4, the fluorescence intensity b is the highest, and the difference from the fluorescence intensity a is the smallest when the fluorescent compound 10 is 50 mol % cis-fluorescent compound and 50 mol % trans-fluorescent compound.

The assembly of cis-fluorescent compound and trans-fluorescent compound contains the same number of moles of cis-fluorescent compound and trans-fluorescent compounds. Specifically, all the cis-fluorescent compound and all the trans-fluorescent compound form the assembly in a fluorescent compound that is 50 mol % cis-fluorescent compound and 50 mol % trans-fluorescent compound. As a rule, the fluorescence intensity of the fluorescence emitted by a fluorescent compound dissolved in a solvent increases as the fluorescent compound concentration increases. Accordingly, the fluorescence intensity b of the fluorescence emitted by the freshness marker 1 increases when all the cis-fluorescent compounds and all the trans-fluorescent compounds form the assembly. This makes the ratio of fluorescence intensity a smaller relative to the fluorescence intensity b, and makes the freshness determination difficult.

On the other hand, the fluorescent compound 10 containing a larger fraction of cis-fluorescent compounds or trans-fluorescent compounds contains cis-fluorescent compounds or trans-fluorescent compounds that do not form the assembly, and accordingly the fraction of the assembly formed by cis-fluorescent compounds and trans-fluorescent compound becomes smaller. The freshness marker 1 using such fluorescent compound 10 has a smaller fluorescence intensity b, and the ratio of fluorescence intensity a increases relative to the fluorescence intensity b. The freshness marker 1 using such fluorescent compound 10 is therefore advantageous for freshness determination.

For example, the fluorescent compound 10 synthesized from 4-benzoylbenzoic acid is dissolved in a solvent to produce a 500 µM (molar concentration) solution, and a 6 molar equivalent of spermidine is added. When the fluorescent compound 10 is 50 mol % cis-fluorescent compound and 50 mol % trans-fluorescent compound, the fluorescence intensity a is higher than the fluorescence intensity b by a factor of 48. On the other hand, when the fluorescent compound 10 is 15 mol % cis-fluorescent compound and 85 mol % trans-fluorescent compound, the fluorescence intensity a is higher than the fluorescence intensity b by a factor of 83. When the fluorescent compound 10 is 95 mol % cis-fluorescent compound and 5 mol % trans-fluorescent compound, the fluorescence intensity a is higher than the fluorescence intensity b by a factor of 86. As shown by these numbers, the freshness marker 1 using the fluorescent compound 10 having a larger fraction of cis-fluorescent compounds or trans-fluorescent compounds has a larger ratio of fluorescence intensity a relative to fluorescence intensity b, and is advantageous for freshness determination.

The cis-fluorescent compound and the trans-fluorescent compound are formed by bonds represented by the following structural formulae (4) and (5), respectively, and the fluorescence characteristics are different. The structural formulae (4) and (5) show simplified structures without structures such as the benzene ring.

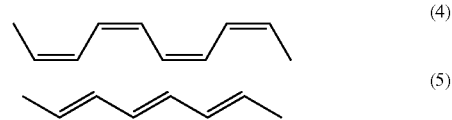

The cis-fluorescent compound contains aryls that are adjacent to each other, and the aryl rotation is restricted. This increases the fluorescence intensity of the emitted fluorescence. On the other hand, the aryls in the trans-fluorescent compound are on opposite sides of the double bond, and the aryl rotation is less restricted than in the cis-fluorescent compound. The fluorescence intensity of the emitted fluorescence is accordingly lower than in the cis-fluorescent compound.

Figure 5:
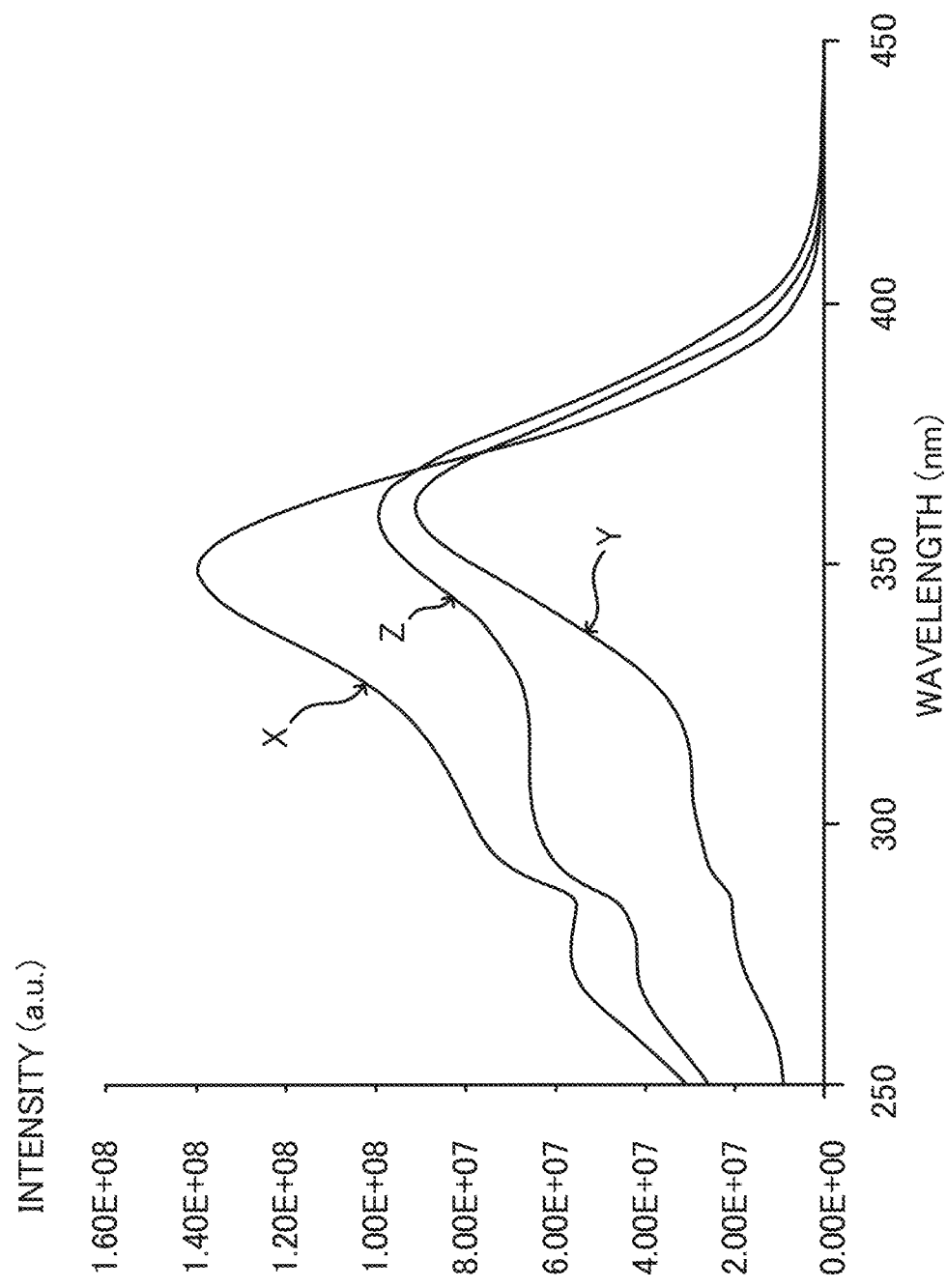
FIG. 5 is a diagram representing the relationship between wavelength and the fluorescence intensity of a fluorescent compound of an Example.

FIG. 5 is a graph representing the relationship between wavelength and the fluorescence intensities of fluorescent compounds according to Examples. The characteristics curve X represents the relationship between wavelength and the fluorescence intensity of the fluorescent compound 10 of primarily cis-fluorescent compound with a cis-fluorescent compound fraction of 95 mol % and a trans-fluorescent compound fraction of 5 mol %. The characteristics curve Y represents the relationship between wavelength and the fluorescence intensity of the fluorescent compound 10 of primarily trans-fluorescent compounds with a cis-fluorescent compound fraction of 15 mol % and a trans-fluorescent compound fraction of 85 mol %. The characteristics curve Z represents the relationship between wavelength and the fluorescence intensity of the fluorescent compound 10 that is 50 mol % cis-fluorescent compound and 50 mol % trans-fluorescent compound.

By comparing the characteristics curves X and Y, the fluorescence intensity represented by the characteristics curve X is higher than the fluorescence intensity represented by the characteristics curve Y. That is, the fluorescent compound 10 containing a larger fraction of cis-fluorescent compounds than trans-fluorescent compounds produces a higher fluorescence intensity a than the fluorescent compound 10 containing a larger fraction of trans-fluorescent compounds than cis-fluorescent compounds.

When the fluorescence characteristics changes of the freshness marker 1 are observable by visual inspection of the freshness marker 1, the freshness can be determined by a simple method without using a digital camera or other devices. Fluorescent compounds 10 containing different fractions of cis-fluorescent compounds were used to produce different freshness markers 1, and the freshness markers 1 were visually observed for fluorescence emission. The visual inspection confirmed brighter fluorescence in the fluorescent compound 10 that contained twice as much cis-fluorescent compound as trans-fluorescent compound than in the fluorescent compound 10 that was 50 mol % cis-fluorescent compound and 50 mol % trans-fluorescent compound. The visual inspection also confirmed much brighter fluorescence in the fluorescent compound 10 that contained cis-fluorescent compounds in three times the amount of the trans-fluorescent compounds than in the fluorescent compound 10 that was 50 mol % cis-fluorescent compound and 50 mol % trans-fluorescent compound.

It is therefore preferable that the freshness marker 1 use the fluorescent compound 10 that contains a larger fraction of cis-fluorescent compounds than trans-fluorescent compounds. More preferably, the fluorescent compound 10 contains at least twice as much cis-fluorescent compound than trans-fluorescent compound. It is further preferable to use the fluorescent compound 10 that contains the cis-fluorescent compound in at least three times the amount of the trans-fluorescent compound.

The exemplary embodiment is described below in greater detail using Examples and Comparative Examples. The following descriptions are not to be construed as limiting.

Freshness markers of Examples 1 to 3 and Comparative Example 1 were produced using a fluorescent compound containing the cis-fluorescent compound represented by the following general formula (6), and the trans-fluorescent compound represented by the following general formula (7), and a fluorescent compound having two cis structures represented by the following general formula (8). As used herein, "cis structure" refers to a structure in which the carboxyl groups, or substituents containing carboxyl groups are disposed on the adjacent benzene rings.

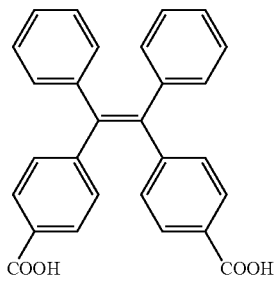

(6)

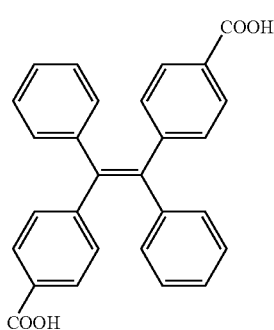

(7)

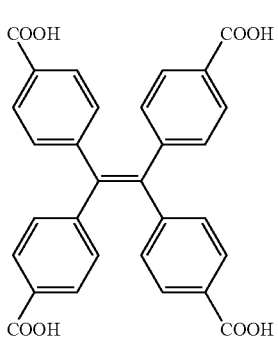

(8)

The cis-fluorescent compound represented by the general formula (6) is the cis-fluorescent compound of general formula (1) of when $R_1$ and $R_2$ are carboxyl groups, and $R_3$ and $R_4$ are hydrogen atoms. The trans-fluorescent compound represented by the general formula (7) is the trans-fluorescent compound of general formula (2) of when $R_5$ and $R_8$ are carboxyl groups, and $R_6$ and $R_7$ are hydrogen atoms. The fluorescent compound represented by the general formula (8) is the fluorescent compound of general formula (1) of when $R_1$, $R_2$, $R_3$, and $R_4$ are carboxyl groups.

Example 1

The cis-fluorescent compound represented by the general formula (6) was separated and purified from a fluorescent compound containing the cis-fluorescent compound of general formula (6) and the trans-fluorescent compound of general formula (7). Known recrystallization and column chromatography techniques were used for the separation and purification of the cis-fluorescent compound. The fluorescent compound was 95 mol % cis-fluorescent compound, and 5 mol % trans-fluorescent compound.

The fractions of the cis-fluorescent compound and the trans-fluorescent compound were determined from the peak area ratio of high-performance liquid chromatography (HPLC).

The fluorescent compound was dissolved in triethylene glycol dimethyl ether to prepare a 500 μM solution (freshness marker 1), and the fluorescence spectrum was measured. The fluorescence spectrum was measured again after adding a 6 molar equivalent of spermidine to the freshness marker 1. The fluorescence intensity a of the freshness marker 1 after the addition of spermidine was 86 times higher than the fluorescence intensity b of the freshness marker 1 before addition of spermidine.

Example 2

The trans-fluorescent compound represented by the general formula (7) was separated and purified from a fluorescent compound containing the cis-fluorescent compound of general formula (6) and the trans-fluorescent compound of general formula (7). Known recrystallization and column chromatography techniques were used for the separation and purification of the trans-fluorescent compound. The fluorescent compound was 15 mol % cis-fluorescent compound, and 85 mol % trans-fluorescent compound.

The fluorescent compound was dissolved in triethylene glycol dimethyl ether to prepare a 500 μM solution (freshness marker 1), and the fluorescence spectrum was measured. The fluorescence spectrum was measured again after adding a 6 molar equivalent of spermidine to the freshness marker 1. The fluorescence intensity a of the freshness marker 1 after the addition of spermidine was 83 times higher than the fluorescence intensity b of the freshness marker 1 before addition of spermidine.

Example 3

The fluorescent compound containing two cis structures represented by the general formula (8) was dissolved in triethylene glycol dimethyl ether to prepare a 500 μM solution (freshness marker 1), and the fluorescence spectrum was measured. The fluorescence spectrum was measured again after adding a 2 molar equivalent of spermidine to the freshness marker 1. The fluorescence intensity a of the freshness marker 1 after the addition of spermidine was 26 times higher than the fluorescence intensity b of the freshness marker 1 before addition of spermidine.

Comparative Example 1

The fluorescent compound containing the cis-fluorescent compound of general formula (6) and the trans-fluorescent compound of general formula (7) was dissolved in triethylene glycol dimethyl ether to prepare a 500 μM solution (freshness marker 1), and the fluorescence spectrum was measured. The fluorescent compound was 50 mol % cis-fluorescent compound, and 50 mol % trans-fluorescent compound. The fluorescence spectrum was measured again after adding a 6 molar equivalent of spermidine to the freshness marker 1. The fluorescence intensity a of the freshness marker 1 after the addition of spermidine was 48 times higher than the fluorescence intensity b of the freshness marker 1 before addition of spermidine.

Table 1 shows the ratios of fluorescence intensities before and after addition of spermidine for the freshness markers 1 of Examples 1 to 3 and Comparative Example 1. The fluorescence intensity ratio is represented as a ratio of fluorescence intensity a after the addition of spermidine relative to the fluorescence intensity b before addition of spermidine (a/b).

TABLE 1

|  | Fluorescence intensity ratio |
| --- | --- |
| Example 1 | 86 |
| Example 2 | 83 |
| Example 3 | 26 |
| Comparative Example 1 | 48 |

Figure 6:
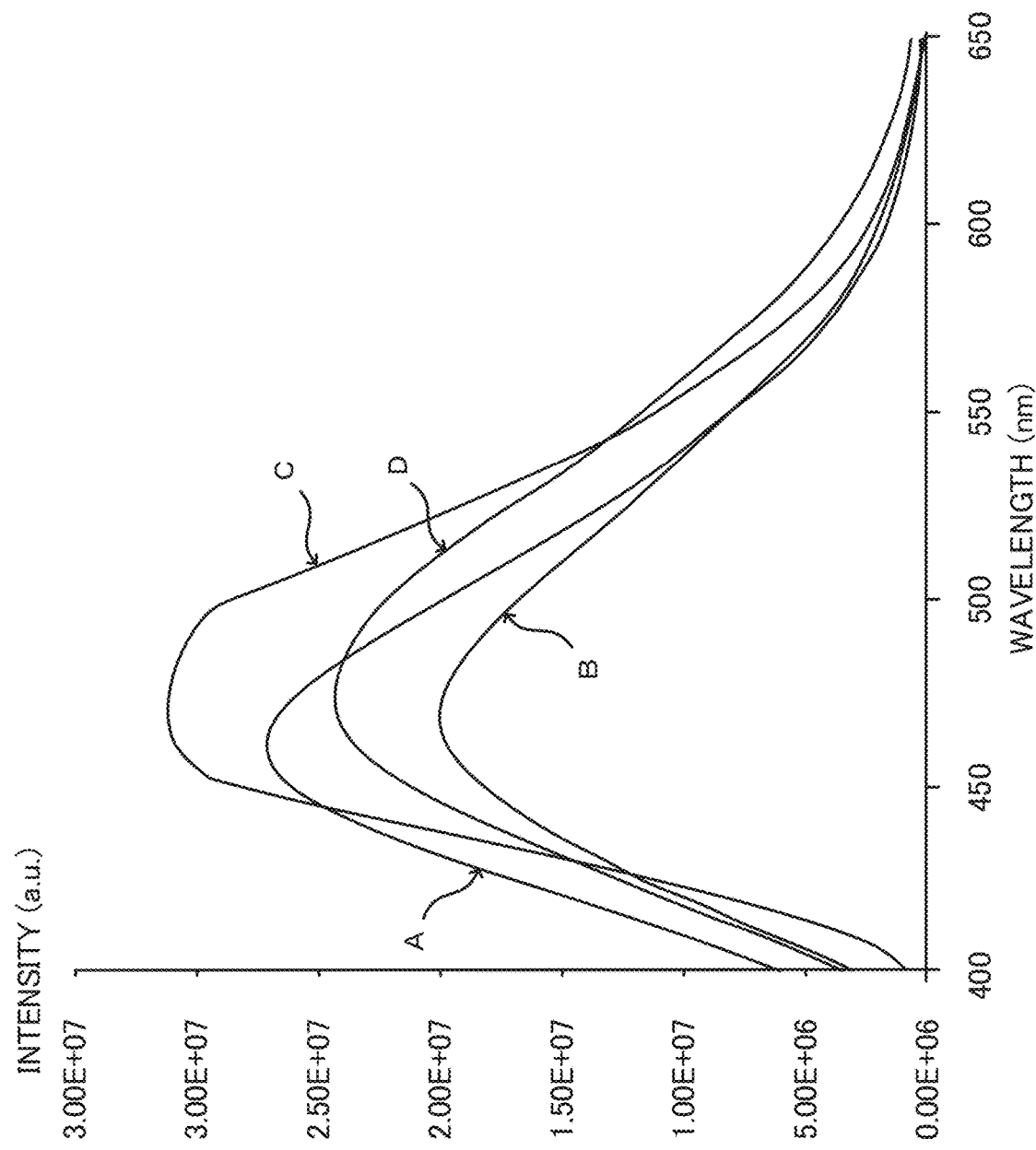
FIG. 6 is a diagram representing the fluorescence intensity of the fluorescence emitted by a fluorescent compound according to an exemplary embodiment after addition of spermidine.

FIG. 6 is a diagram representing the fluorescence intensities a of the freshness markers 1 of Examples 1 to 3 and Comparative Example 1 after addition of spermidine. In FIG. 6, curve A represents the fluorescence intensity a of the freshness marker 1 of Example 1 after addition of spermidine, curve B represents the fluorescence intensity a of the freshness marker 1 of Example 2 after addition of spermidine, curve C represents the fluorescence intensity a of the freshness marker 1 of Example 3 after addition of spermidine, and curve D represents the fluorescence intensity a of the freshness marker 1 of Comparative Example 1 after addition of spermidine.

The wavelength at which the highest fluorescence intensity occurs in the fluorescence spectrum differs for different fluorescent compound structures. The peak of the fluorescence spectrum for the freshness marker 1 of Comparative Example 1 occurs more toward the longer wavelength side as compared to the peak of the fluorescence spectrum for the freshness markers 1 of Examples 1 and 2. This difference in the peak position of the fluorescence spectrum is suggestive of formation of a cis- and trans-fluorescent compound assembly in the freshness marker 1 of Comparative Example 1.

As shown in Table 1 and FIG. 6, the freshness marker 1 of Example 1 has a higher fluorescence intensity a than the freshness marker 1 of Comparative Example 1, and the ratio of fluorescence intensity a relative to the fluorescence intensity b is also greater. It can therefore be said that the freshness marker 1 of Example 1 has higher spermidine sensitivity.

As shown in Table 1 and FIG. 6, the freshness marker 1 of Example 2 has a smaller fluorescence intensity a than the freshness marker 1 of Comparative Example 1, but has a larger ratio of fluorescence intensity a relative to the fluorescence intensity b. It can be said from this that the freshness marker 1 of Example 2 has high spermidine sensitivity.

In the freshness marker 1 of Example 3, spermidine was added to the freshness marker 1 in ⅓ of the amount added to the freshness markers 1 of Examples 1 and 2 and Comparative Example 1. The ratio of fluorescence intensity a relative to the fluorescence intensity b was 26, smaller than that of the freshness marker 1 of Comparative Example 1. However, a ratio of 70 or higher can be expected when the freshness marker 1 is equimolar. As shown in FIG. 6, the freshness marker 1 of Example 3 has the highest fluorescence intensity a compared to Examples 1 and 2 and Comparative Example 1. It can be said from this that the freshness marker 1 of Example 3 has high spermidine sensitivity.

From these evaluation results, it can be said that the freshness markers using fluorescent compounds containing a larger fraction of cis-fluorescent compounds or trans-fluorescent compounds, and the freshness marker using a fluorescent compound containing two cis structures have high spermidine sensitivity.

The freshness markers 1 of Examples 1 and 2 and Comparative Example 1 were used to produce freshness labels of Examples 4 and 5, and Comparative Examples 2 and 3.

Figure 7A:
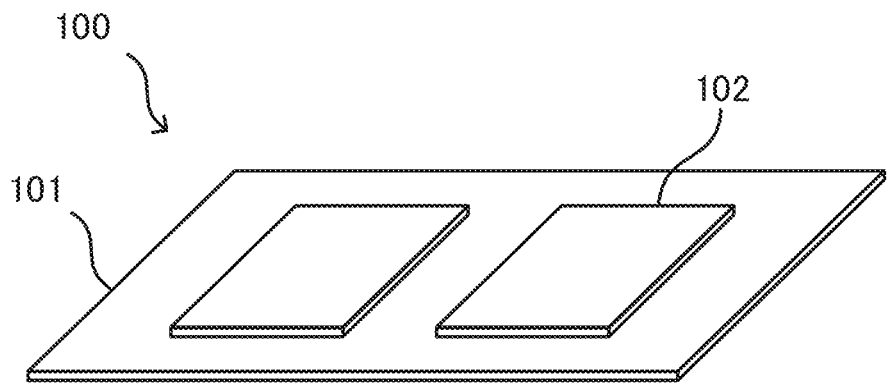
FIG. 7A is a diagram explaining a fabrication method of a freshness label according to an exemplary embodiment.
Figure 7B:
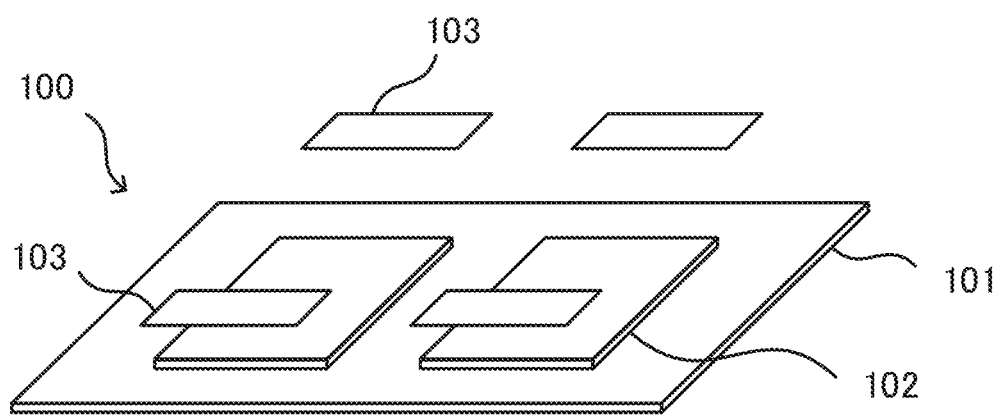
FIG. 7B is a diagram explaining a fabrication method of a freshness label according to an exemplary embodiment.
Figure 7C:
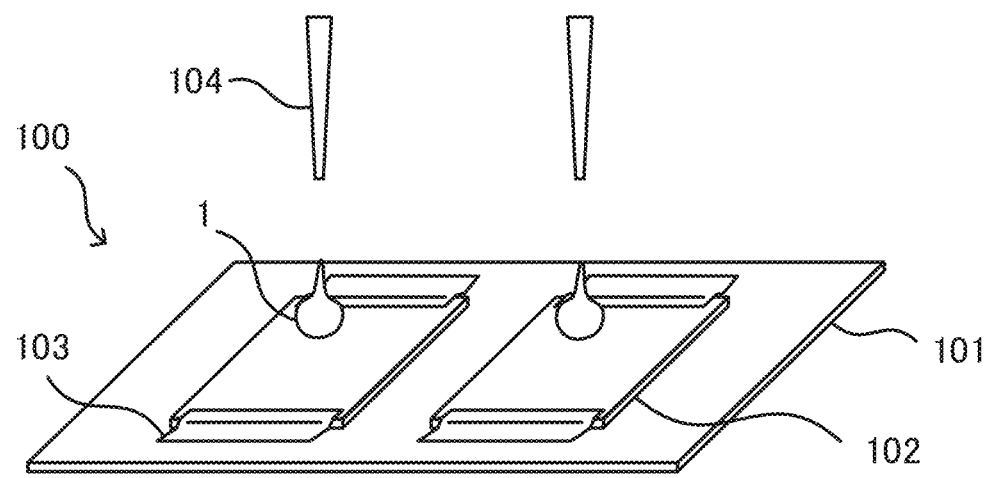
FIG. 7C is a diagram explaining a fabrication method of a freshness label according to an exemplary embodiment.

FIGS. 7A, 7B, and 7C are diagrams representing a fabrication method of the freshness label 100.

First, as shown in FIG. 7A, glass filters 102 were installed on a glass sheet 101, and the both ends of the glass filters 102 were fixed with an adhesive tape 103, as shown in FIG. 7B.

Thereafter, as shown in FIG. 7C, the freshness marker 1 was dropped with a pipette 104, and the glass filters 102 were impregnated with the freshness marker 1 to fabricate the freshness label 100. Example 4 is the freshness label 100 fabricated with the freshness marker 1 of Example 1. Example 5 is the freshness label 100 fabricated with the freshness marker 1 of Example 2. Comparative Examples 2 and 3 are the freshness labels 100 fabricated with the freshness marker 1 of Comparative Example 1.

Figure 8:
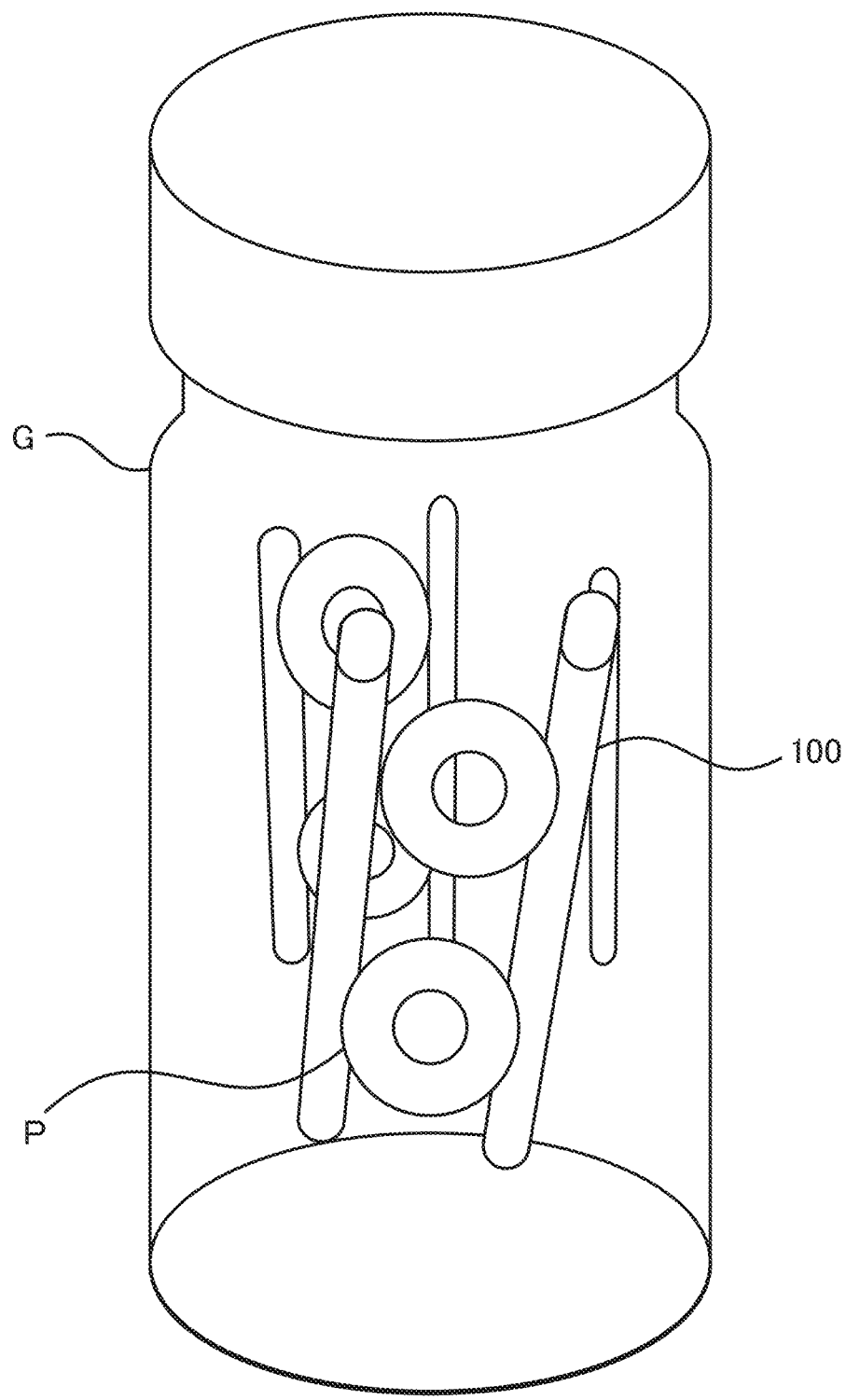
FIG. 8 is a diagram explaining an evaluation method for a freshness label according to an exemplary embodiment.

As illustrated in FIG. 8, the freshness label 100 fabricated in the manner described above was installed in a lidded bottle container H containing a fresh food product P (e.g., kamaboko; minced and steamed fish meat). Here, the freshness label 100 was installed without contacting the food product P. After installing the freshness label 100, the container was closed, and stored in a room temperature environment. The freshness label 100 was then observed for fluorescence state over a time period.

The fluorescence observation was conducted by observing a digital camera image of the fluorescence state after the freshness label 100 was taken out of the bottle container H, and irradiated with UV light in a room where the influence of visible light was small.

FIG. 9 shows images of the freshness labels of Comparative Examples 2 and 3, the freshness label of Example 4, and the freshness label of Example 5 after 1, 2, 3, 4, and 5 days. A fluorescence intensity change was visually observable by day 3 in the freshness label of Example 4, and by day 4 in the freshness label of Example 5, demonstrating that the fluorescence intensities of Examples 4 and 5 were higher than the fluorescence intensities of the freshness labels of Comparative Examples 2 and 3.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A fluorescent compound mixture, comprising:
   a first fluorescent compound of a structure represented by the following general formula (1); and
   a second fluorescent compound of a structure represented by the following general formula (2), wherein
   the number of moles of the first fluorescent compound in the fluorescent compound mixture is larger than the number of moles of the second fluorescent compound in the fluorescent compound mixture,
   the fluorescent compound mixture has fluorescence characteristics that vary in the presence of a subject substance,
   general formula (1) is:

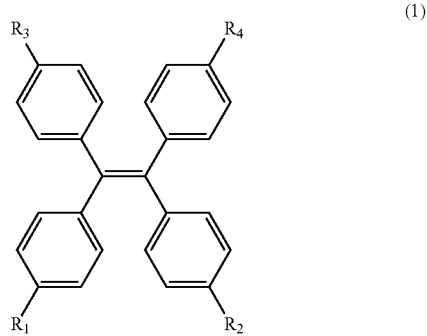

(1)

wherein
   $R_1$ and $R_2$ each independently represent a carboxyl group, or a substituent containing a carboxyl group, the substituent containing a carboxyl group is at least one of —$(CH_2)_m$—COOH, —O—$(CH_2)_m$—COOH, —S—$(CH_2)_m$—COOH, —NH—$(CH_2)_m$—COOH, —O—$(CH_2)_m$—S—$(CH_2)_n$—COOH, —O—$(CH_2)_m$—NH—$(CH_2)_n$—COOH, —S—$(CH_2)_m$—O—$(CH_2)_m$—COOH, —S—$(CH_2)_m$—NH—$(CH_2)_n$—COOH, —NH—$(CH_2)_m$—O—$(CH_2)_n$—COOH, —NH—$(CH_2)_m$—S—$(CH_2)_n$—COOH, where m and n each independently represent an integer in a range of 1 to 6, and
   $R_3$ and $R_4$ each independently represent a hydrogen atom, an alkyl group, an alkoxy group, a halogen atom, a hydroxyl group, a carboxyl group, or a substituent containing a carboxyl group,
general formula (2) is:

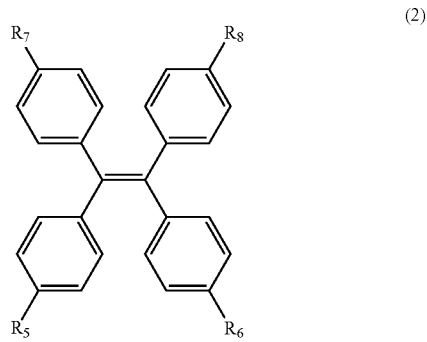

(2)

wherein
   $R_5$ and $R_8$ each independently represent a carboxyl group, or a substituent containing a carboxyl group, the substituent containing a carboxyl group is at least one of —$(CH_2)_m$—COOH, —O—$(CH_2)_m$—COOH, —S—$(CH_2)_m$—COOH, —NH—$(CH_2)_m$—COOH, —O—$(CH_2)_m$—S—$(CH_2)_n$—COOH, —O—$(CH_2)_m$—NH—$(CH_2)_n$—COOH, —S—$(CH_2)_m$—O—$(CH_2)_m$—COOH, —S—$(CH_2)_m$—NH—$(CH_2)_n$—COOH, —NH—$(CH_2)_m$—O—$(CH_2)_n$—COOH, —NH—$(CH_2)_m$—S—$(CH_2)_n$—COOH where m and n each independently represent an integer in a range of 1 to 6, and $R_6$ and $R_7$ each independently represent a hydrogen atom, an alkyl group, an alkoxy group, a halogen atom, a hydroxyl group, a carboxyl group, or a substituent containing a carboxyl group, and the second fluorescent compound does not have the same structure as the first fluorescent compound.

2. A freshness marker for sensing a subject substance, comprising:
the fluorescent compound mixture of claim 1; and
a solvent in which the fluorescent compound mixture is dissolved.

3. The freshness marker according to claim 2, wherein the number of moles of the first fluorescent compound in the fluorescent compound mixture is at least twice the number of moles of the second fluorescent compound in the fluorescent compound mixture.

4. The freshness marker according to claim 2, wherein the first fluorescent compound and the second fluorescent compound form an assembly in the solvent, and the number of moles of the first fluorescent compound in the solvent and remaining unassembled is at least twice the number of moles of the first fluorescent compound in the assembly.

5. A freshness label, comprising:
a freshness marker comprising the fluorescent compound mixture of claim 1; and
a medium retaining the freshness marker.

6. A sensing system, comprising:
a freshness marker comprising the fluorescent compound mixture of claim 1;
an ultraviolet source unit that emits ultraviolet light towards the freshness marker; and
an emission detector that senses the subject substance using an image pattern generated by exposing the freshness marker to ultraviolet light.

7. The sensing system according to claim 6, wherein the emission detector determines a ratio of luminescence intensities in the image pattern in the presence and absence of the subject substance to sense the subject substance.

8. The sensing system according to claim 6, wherein the emission detector determines a difference between luminescence intensities in the image pattern in the presence and absence of the subject substance to sense the subject substance.

9. A freshness label, comprising:
the freshness marker of claim 2; and
a medium retaining the freshness marker.

10. The fluorescent compound mixture of claim 1, wherein
$R_3$ is an alkyl group, an alkoxy group, a halogen atom, a hydroxyl group, a carboxyl group, or a substituent containing a carboxyl group,
$R_4$ is an alkyl group, an alkoxy group, a halogen atom, a hydroxyl group, a carboxyl group, or a substituent containing a carboxyl group,
$R_6$ is an alkyl group, an alkoxy group, a halogen atom, a hydroxyl group, a carboxyl group, or a substituent containing a carboxyl group, and
$R_7$ is an alkyl group, an alkoxy group, a halogen atom, a hydroxyl group, a carboxyl group, or a substituent containing a carboxyl group.

11. A fluorescent compound mixture, comprising:
a first fluorescent compound of a structure represented by the following general formula (1); and
a second fluorescent compound of a structure represented by the following general formula (2), wherein
the number of moles of the first fluorescent compound in the fluorescent compound mixture is larger than the number of moles of the second fluorescent compound in the fluorescent compound mixture, the fluorescent compound mixture has fluorescence characteristics that vary in the presence of a subject substance, general formula (1) is:

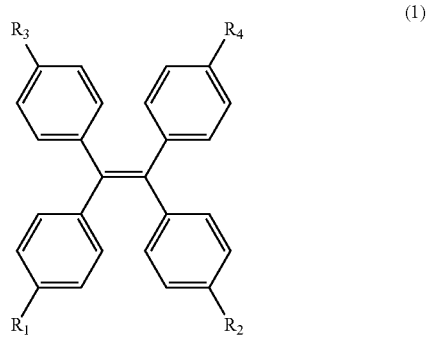

wherein $R_1$ and $R_2$ each independently represent a carboxyl group or a substituent containing a carboxyl group, and $R_3$ and $R_4$ each independently represent an alkyl group, an alkoxy group, a halogen atom, a hydroxyl group, a carboxyl group, or a substituent containing a carboxyl group, general formula (2) is:

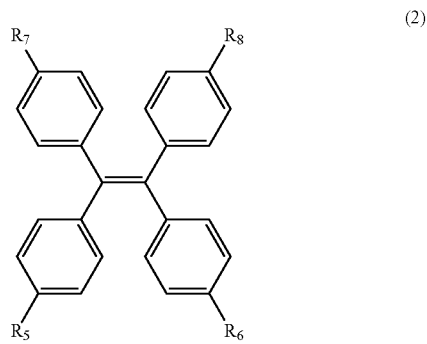

wherein $R_5$ and $R_8$ each independently represent a carboxyl group or a substituent containing a carboxyl group, and $R_6$ and $R_7$ each independently represent an alkyl group, an alkoxy group, a halogen atom, a hydroxyl group, a carboxyl group, or a substituent containing a carboxyl group, and the second fluorescent compound does not have the same structure as the first fluorescent compound.

12. A freshness marker for sensing a subject substance, the freshness marker comprising:
the fluorescent compound mixture of claim 11; and
a solvent in which the fluorescent compound mixture is dissolved.

13. The freshness marker according to claim 12, wherein the number of moles of the first fluorescent compound in the fluorescent compound mixture is at least twice the number of moles of the second fluorescent compound in the fluorescent compound mixture.

14. The freshness marker according to claim 12, wherein the first fluorescent compound and the second fluorescent compound form an assembly in the solvent, and the number of moles of the first fluorescent compound in the solvent and remaining unassembled is at least twice the number of moles of the first fluorescent compound in the assembly.

15. A freshness label, comprising:
a freshness marker comprising the fluorescent compound mixture of claim 11; and
a medium retaining the freshness marker.

16. A sensing system, comprising:
a freshness marker comprising the fluorescent compound mixture of claim 11;
an ultraviolet source unit that emits ultraviolet light towards the freshness marker; and
an emission detector that senses the subject substance using an image pattern generated by exposing the freshness marker to ultraviolet light.

17. The sensing system according to claim 16, wherein the emission detector determines a ratio of luminescence intensities in the image pattern in the presence and absence of the subject substance to sense the subject substance.

18. The sensing system according to claim 16, wherein the emission detector determines a difference between luminescence intensities in the image pattern in the presence and absence of the subject substance to sense the subject substance.

19. A freshness label, comprising:
the freshness marker of claim 12; and
a medium retaining the freshness marker.

20. The fluorescent compound mixture of claim 11, wherein
$R_3$ is a halogen atom, a hydroxyl group, a carboxyl group, or a substituent containing a carboxyl group,
$R_4$ is a halogen atom, a hydroxyl group, a carboxyl group, or a substituent containing a carboxyl group,
$R_6$ is a halogen atom, a hydroxyl group, a carboxyl group, or a substituent containing a carboxyl group, and
$R_7$ is a halogen atom, a hydroxyl group, a carboxyl group, or a substituent containing a carboxyl group.

* * * * *